US00PP08108P

United States Patent [19]

VandenBerg

[11] Patent Number: Plant 8,108

[45] Date of Patent: Jan. 19, 1993

[54] CHRYSANTHEMUM PLANT NAMED MAMBO

[75] Inventor: Cornelis P. VandenBerg, Salinas, Calif.

[73] Assignee: Yoder Brothers, Inc., Barberton, Ohio

[21] Appl. No.: 715,631

[22] Filed: Jun. 14, 1991

[51] Int. Cl.[5] ..... A01H 5/00

[52] U.S. Cl. ..... Plt./82.3

[58] Field of Search ..... Plt./82.2, 82.3, 74, Plt./74.1, 79

*Primary Examiner*—Howard J. Locker

*Attorney, Agent, or Firm*—Foley & Lardner

[57] ABSTRACT

A Chrysanthemum plant named Mambo particularly characterized by its flat capitulum form; anemone capitulum type; orange-bronze ray floret color; diameter across face of capitulum of 64 to 76 mm when fully opened, when grown as a single stem spray cut mum; flowering response in Salinas under normal temperatures is 51 to 54 days after start of short days, and flowering response in Bogota, Colombia under temperatures of minimum 6.3 degrees Celsius night and maximum 29 degrees Celsius day is 64 to 65 days; plant height is 94 to 107 cm when grown in Salinas with 6 to 7 long days prior to start of short days, and 94 to 140 cm when grown in Bogota with 7 to 17 long days prior to start of short days; peduncle length of the first lateral at flowering after removing the apical bud without growth regulator applications is 8 to 13 cm when grown in Salinas, and 5 to 10 cm when grown in Bogota; peduncle length of the fourth lateral at flowering is 13 to 18 cm when grown both in Salinas and in Bogota, and excellent tolerance to low night temperatures for bud initiation and flower development.

3 Drawing Sheets

1

The present invention comprises a new and distinct cultivar of Chrysanthemum, botanically known as *Dendranthema grandiflora*, and referred to by the cultivar name Mambo.

Mambo, identified as 1661 (87-401001), was originated from a cross made by Cornelis P. VandenBerg in a controlled breeding program in Salinas, Calif., in August 1986.

The female parent of Mambo was the cultivar Samoa, identified as 5528 (84-112012), which cultivar was introduced in the United Kingdom. Samoa is described as an orange-bronze anemone cut spray mum with a green anemone cushion and having a flowering response to short days of 53 to 64 days when grown in Salinas, Calif., and 68 to 75 days when grown in Bogota, Colombia; a plant height of 91 to 119 cm when grown with 6 to 7 long days prior to start of short days in Salinas, Calif., and 137 to 163 cm with 7 to 14 long days prior to start of short days when grown in Bogota, Colombia; and a diameter of capitulum of 89 to 102 mm. The female parent was discarded from the Colombian program in October 1986 after two trials because of unsatisfactory performance under the Bogota environmental conditions.

The male parent of Mambo was an unnamed seedling, identified as 6883 (84-189006), and described as a bronze daisy spray cut mum having a flowering response to short days of 52 to 63 days in Salinas, Calif., and 66 to 70 days in Bogota, Colombia; and a plant height of 71 to 94 cm with 7 long days prior to start of short days when grown in Salinas, Calif., and 81 to 104 cm with 7 long days prior to start of short days in Bogota, Colombia. The diameter of capitulum of the male parent of Mambo was not recorded. The male parent was discarded from all programs in March 1988.

Mambo was discovered and selected as one flowering plant within the progeny of the stated cross by Cornelis P. VandenBerg in November 1987, in a controlled environment in Salinas, Calif.

2

The first act of asexual reproduction of Mambo was accomplished when vegetative cuttings were taken from the initial selection in January 1988 in a controlled environment in Salinas, Calif., by technicians working under supervision of Cornelis P. VandenBerg.

Horticultural examination of controlled flowerings of successive plantings has shown that the unique combination of characteristics as herein disclosed for Mambo are firmly fixed and are retained through successive generations of asexual reproduction.

Mambo has not been observed under all possible environmental conditions. The phenotype may vary significantly with variations in environment such as temperature, light intensity and daylength.

The following observations, measurements and comparisons describe plants grown in Salinas, Calif., and in Bogota, Colombia, under greenhouse conditions which approximate those generally used in commercial greenhouse practice. The low temperature tolerance was determined in repeated flowerings in Bogota, Colombia, with an average minimum low night temperature inside the greenhouse during our trials ranging from 6.3 to 10.0 degrees Celsius.

The following traits have been repeatedly observed and are determined to be basic characteristics of Mambo, which, in combination, distinguish this Chrysanthemum as a new and distinct cultivar:

1. Flat capitulum form.
2. Anemone capitulum type.
3. Orange-bronze ray floret color.
4. Diameter across face of capitulum of 64 to 76 mm when fully opened, when grown as a single stem spray cut mum.
5. Flowering response in Salinas under normal temperatures is 51 to 54 days after start of short days. Flowering response in Bogota, Colombia under temperatures of minimum 6.3 degrees Celsius night and maximum 29 degrees Celsius day is 64 to 65 days.

6. Plant height is 94 to 107 cm when grown in Salinas with 6 to 7 long days prior to start of short days; and 94 to 140 cm when grown in Bogota with 7 to 17 long days prior to start of short days.
7. Peduncle length of the first lateral at flowering after removing the apical bud without growth regulator applications is 8 to 13 cm when grown both in Salinas and in Bogota. Peduncle length of the fourth lateral at flowering is 13 to 18 cm when grown both in Salinas and in Bogota.
8. Excellent tolerance to low night temperatures for bud initiation and flower development.

The accompanying photographic drawings show typical inflorescence and leaf characteristics of Mambo, with the colors being as nearly true as possible with illustrations of this type.

Sheet 1 is a color photograph of Mambo grown as a single stem spray cut mum in Salinas, Calif.

Sheet 2 is a black and white photograph of three views of the inflorescence of Mambo.

Sheet 3 is a black and white photograph showing the upper and under sides of the leaves of Mambo at 3 stages of development (mature, intermediate and immature). In sheets 2 and 3 a measuring tape in centimeters has been added.

Of the commercial cultivars known to the inventor, the most similar in comparison to Mambo is the cultivar identified as Leona, disclosed in U.S. Plant Pat. No. 7,315. Reference is made to attached Chart A, which compares certain characteristics of Mambo to the same characteristics of Leona.

Similar traits are capitulum form and type, and spray formation. Although both Mambo and Leona can be generally described as having an orange-bronze to bronze ray floret color, the color of Mambo is more vibrant than the color of Leona. In comparison to Leona, Mambo has a smaller diameter of capitulum, a slower flowering response after start of short days in Salinas, and a taller plant height when grown in Salinas. The plant height of both cultivars when grown in Bogota is not comparable because of the different long day period given prior to start of short days. The overall peduncle length for Mambo is shorter than the peduncle length of Leona. Low night temperature tolerance of Leona is described as marginal, and Leona is not being produced in Colombia because of this trait, while the low night temperature of Mambo is excellent.

When compared with both parents, Mambo has a slightly faster flowering response in Salinas than either parent, and has a smaller diameter of capitulum than the female parent. In addition, neither parent can be produced commercially in Bogota because of overall unsatisfactory performance, while the overall performance of Mambo in Bogota warrants commercial introduction in Colombia.

In the following description color references are made to The Royal Horticultural Society Colour Chart. The actual color of Mambo is not represented in the RHS Colour Chart, and the color values given for Mambo are those believed closest to the actual color of Mambo. The color values were determined on plant material grown as a single stem spray cut mum in Salinas, Calif. on Jun. 26, 1990.

Classification:

*Botanical.*—*Dendranthema grandiflora* cv Mambo.

*Commercial.*—Anemone spray cut mum.

INFLORESCENCE

A. Capitulum

*Form.*—Flat.

*Type.*—Anemone.

*Diameter across face.*—64 to 76 mm when fully opened.

B. Corolla of ray florets:

*Color (general tonality from a distance of three meters).*—Orange-bronze.

*Color (upper surface).*—Closest to 23B to 24B.

*Color (under surface).*—Closest to 21C.

*Shape.*—Flat, straight. Some tips of ray florets are indented.

C. Corolla of disc florets:

*Color (mature).*—Closest to 26A.

*Color (immature).*—Closest to 26A, with a slight tinge of 151A.

D. Reproductive Organs:

*Androecium.*—Present on disc florets only; moderate pollen.

*Gynoecium.*—Present on both ray and disc florets.

PLANT

A. General appearance:

*Height.*—94 to 107 cm when grown in Salinas with 6 to 7 long days prior to start of short days, and 94 to 140 cm when grown in Bogota with 7 to 17 long days prior to start of short days.

B. Foliage:

*Color (upper surface).*—137A.

*Color (under surface).*—147B.

*Shape.*—See photograph.

CHART A

COMPARISON OF MAMBO AND LEONA

| CHARACTERISTIC | MAMBO | LEONA |
|---|---|---|
| Ray floret color | Orange-bronze | Bronze |
| Capitulum form and type | Flat anemone | Flat anemone |
| Diameter across face of capitulum | 64 to 76 mm | 76 to 90 mm |
| Flowering response: | | |
| in Salinas | 51 to 54 days | 44 to 51 days |
| in Bogota | 64 to 65 days | 60 to 67 days |
| Plant height: | | |
| 6–7 long days Salinas | 94 to 107 cm | 81 to 85 cm |
| 7–17 long days Bogota | 94 to 140 cm | |
| 14 long days Bogota | | 91 to 117 cm |
| Peduncle length: | | |
| 1st lateral Salinas | 8 to 18 cm | 8 to 15 cm |
| 4th lateral Salinas | 13 to 18 cm | 20 to 23 cm |
| 1st lateral Bogota | 5 to 10 cm | 15 to 23 cm |
| 4th lateral Bogota | 13 to 18 cm | 15 to 25 cm |
| Spray formation | Terminal | Terminal |
| Low night temperature | Excellent | Marginal |

COMPARISONS MADE OF PLANTS GROWN AS SINGLE STEM SPRAY CUT MUMS IN SALINAS, CALIFORNIA AND IN BOGOTA, COLOMBIA

I claim:

1. A new and distinct Chrysanthemum plant named Mambo, as described and illustrated.

* * * * *

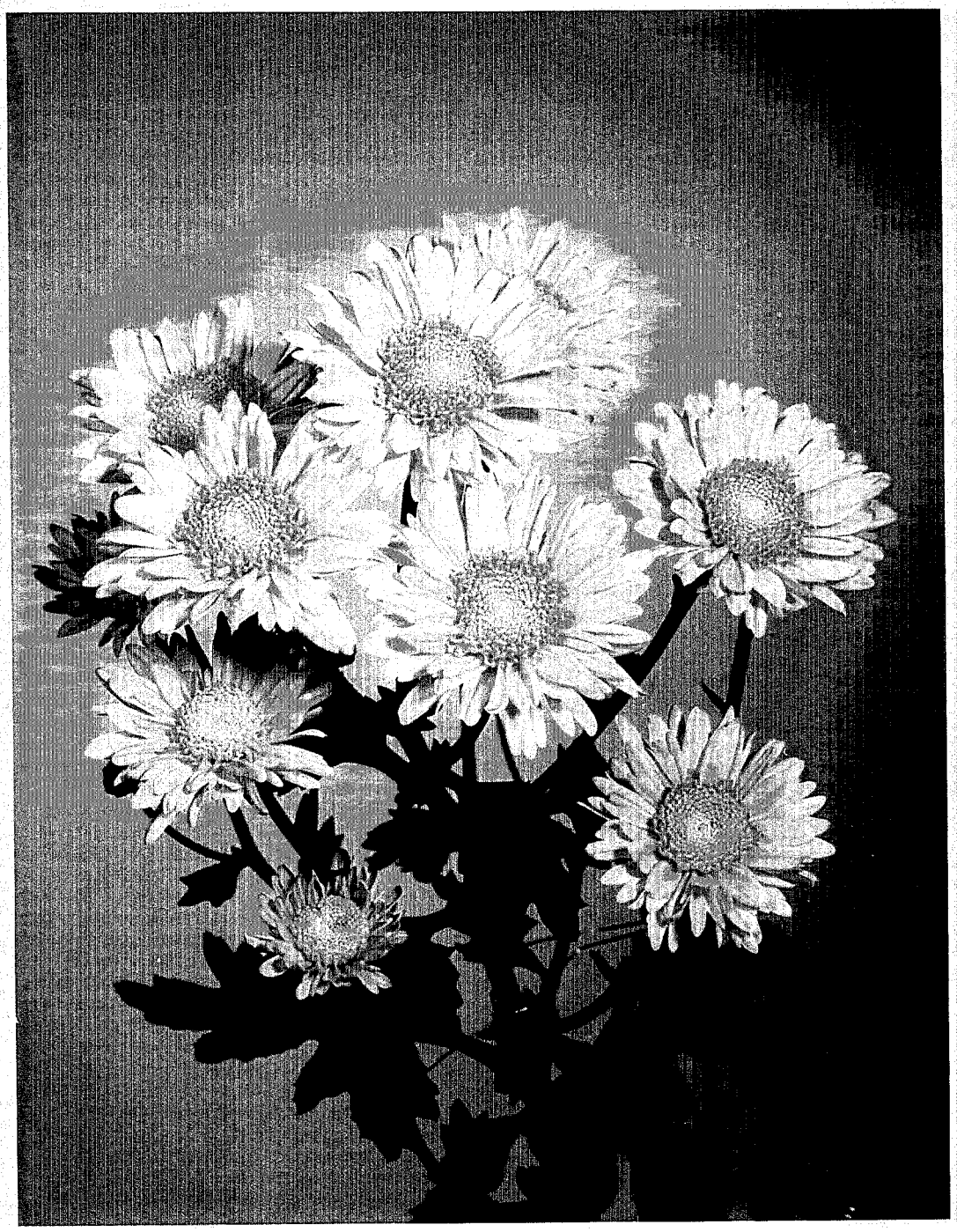

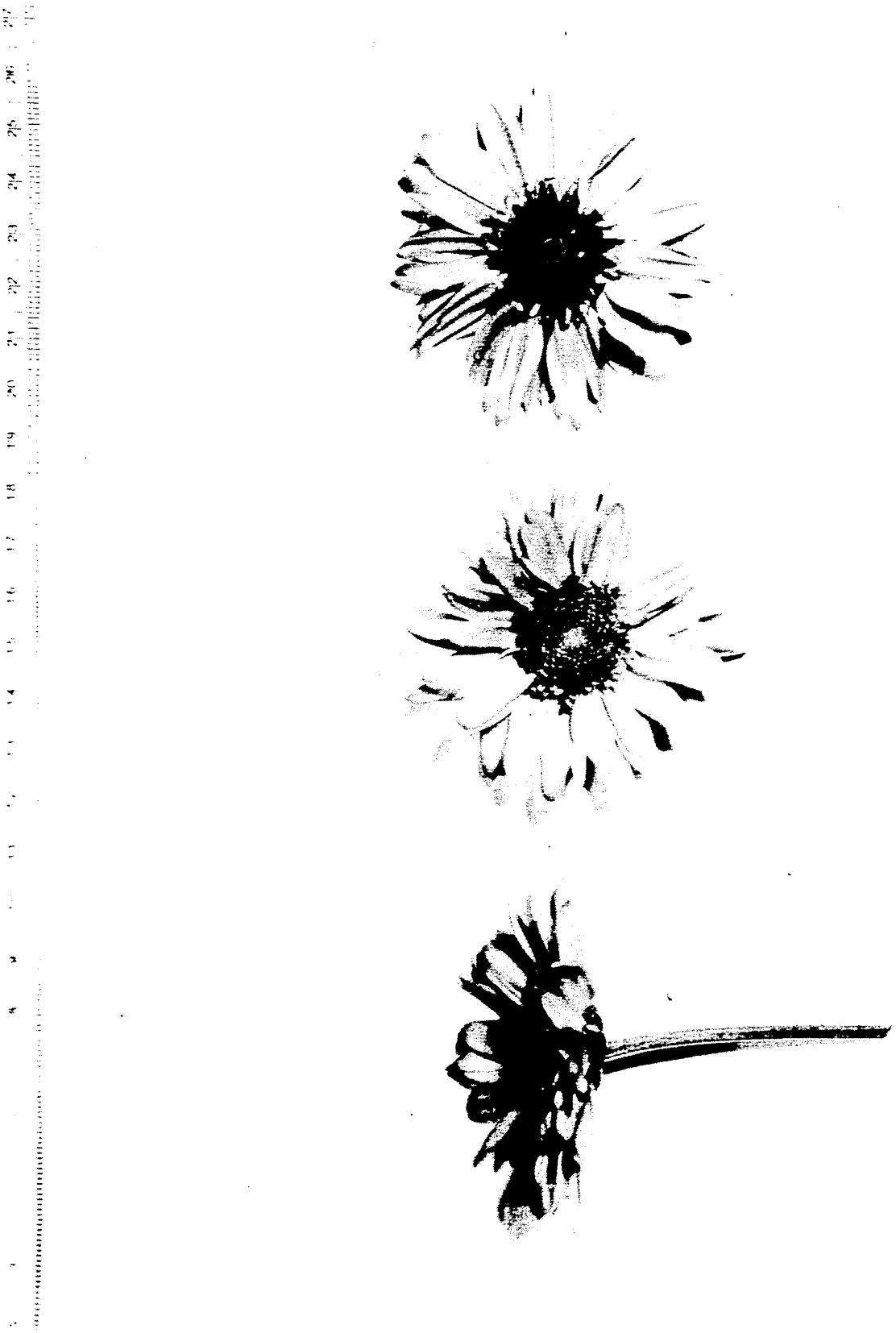

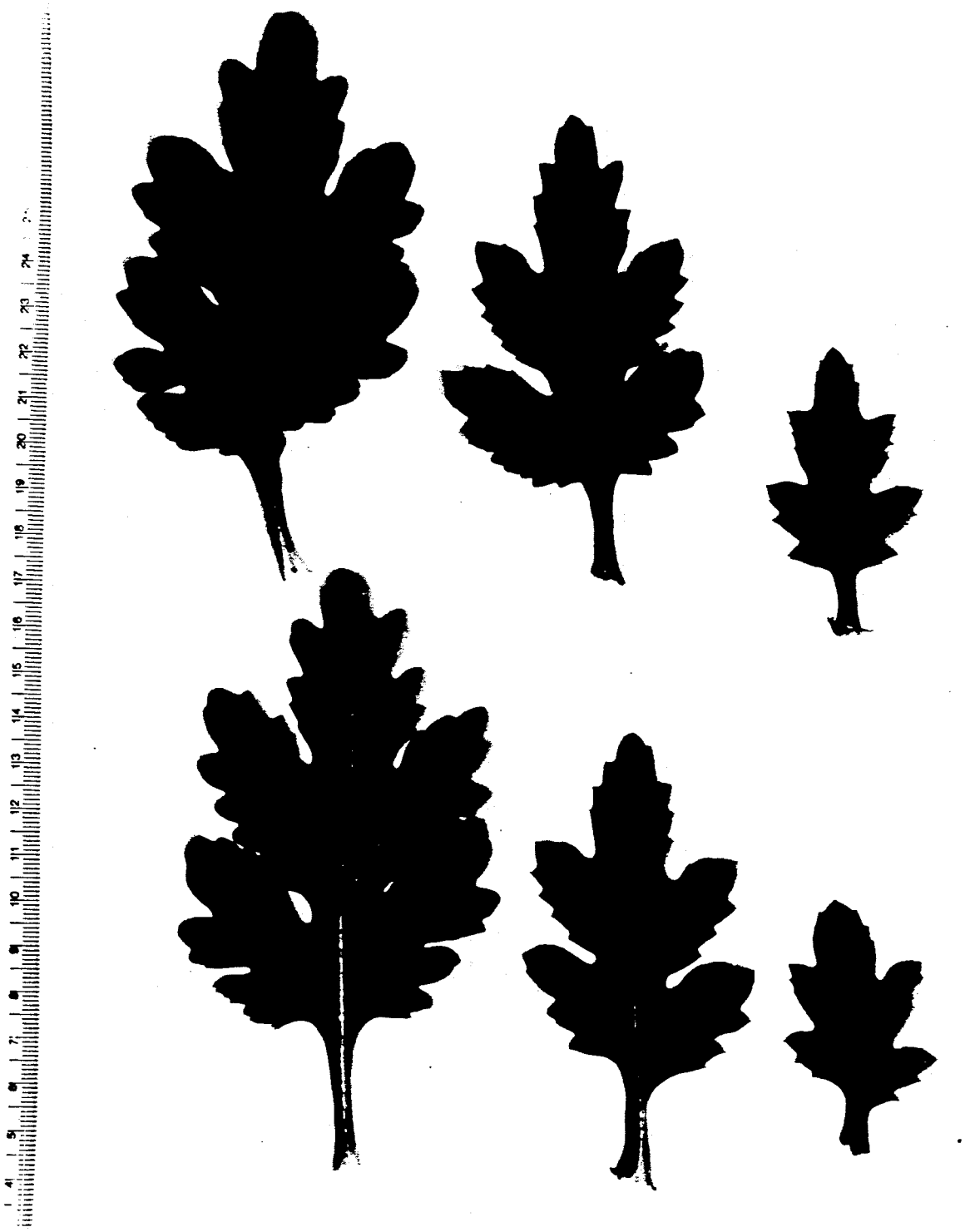

UNITED STATES PATENT AND TRADEMARK OFFICE

CERTIFICATE OF CORRECTION

PATENT NO. : PP 8,108

DATED : January 19, 1993

INVENTOR(S) : Cornelis P. VandenBerg

It is certified that error appears in the above-indentified patent and that said Letters Patent is hereby corrected as shown below:

Column 3, lines 7 and 8, delete "both in Salinas and in Bogota" and insert --in Salinas and 5 to 10 cm when grown in Bogota--.

Column 4, line 52, "8 to 18 cm" under "MAMBO" should read --8 to 13cm--.

Signed and Sealed this

Thirteenth Day of September, 1994

*Attest:*

*Attesting Officer*

Bruce Lehman

BRUCE LEHMAN

*Commissioner of Patents and Trademarks*